(12) United States Patent
Brockway et al.

(10) Patent No.: US 9,706,956 B2
(45) Date of Patent: Jul. 18, 2017

(54) METHOD AND APPARATUS FOR ASSESSING CARDIAC AND/OR MENTAL HEALTH

(71) Applicant: VivaQuant LLC, St. Paul, MN (US)

(72) Inventors: Marina Brockway, St. Paul, MN (US); Brian Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 0 days.

(21) Appl. No.: 15/144,324

(22) Filed: May 2, 2016

(65) Prior Publication Data

US 2016/0317073 A1    Nov. 3, 2016

Related U.S. Application Data

(63) Continuation-in-part of application No. 15/132,373, filed on Apr. 19, 2016, which is a continuation of
(Continued)

(51) Int. Cl.
*A61B 5/16* (2006.01)
*A61B 5/04* (2006.01)
(Continued)

(52) U.S. Cl.
CPC ........... *A61B 5/165* (2013.01); *A61B 5/0006* (2013.01); *A61B 5/021* (2013.01); *A61B 5/026* (2013.01); *A61B 5/02028* (2013.01); *A61B 5/0245* (2013.01); *A61B 5/02055* (2013.01); *A61B 5/02416* (2013.01); *A61B 5/046* (2013.01); *A61B 5/0408* (2013.01); *A61B 5/04012* (2013.01); *A61B 5/04014* (2013.01); *A61B 5/04017* (2013.01); *A61B 5/0452* (2013.01);
(Continued)

(58) Field of Classification Search
None
See application file for complete search history.

(56) References Cited

U.S. PATENT DOCUMENTS 5,090,418 A    2/1992   Squires et al.
5,279,283 A    1/1994   Dillon
(Continued)

FOREIGN PATENT DOCUMENTS

WO   2013/043157 A2   3/2013
WO   2014/123512 A1   8/2014

OTHER PUBLICATIONS

B. Widrow, et al., "Adaptive noise cancelling: principles and applications," IEEE Proc., vol. 63, No. 12, pp. 1692-1716, Dec. 1975.
(Continued)

*Primary Examiner* — Brian T Gedeon
(74) *Attorney, Agent, or Firm* — Crawford Maunu PLLC

(57) ABSTRACT

Aspects of the disclosure are directed to detecting physiological and/or other characteristics of subjects. As may be implemented in accordance with one or more embodiments, a time series of cardiac intervals is computed from a recording of activity of a beating heart of a subject, and the time series is decomposed into subcomponents. An envelope of at least one of the subcomponents is computed, and the presence and/or degree of a depressive or stressed mental state of the subject is detected based upon characteristics of the envelope.

12 Claims, 9 Drawing Sheets

Related U.S. Application Data application No. 14/630,918, filed on Feb. 25, 2015, now Pat. No. 9,314,181, which is a continuation-in-part of application No. 14/230,439, filed on Mar. 31, 2014, now Pat. No. 9,072,438, said application No. 14/230,439 is a continuation of application No. 13/668,898, filed on Nov. 5, 2012, now Pat. No. 8,688,202, which is a continuation-in-part of application No. 12/938,995, filed on Nov. 3, 2010, now Pat. No. 8,632,465, said application No. 13/668,898 is a continuation-in-part of application No. 13/172,415, filed on Jun. 29, 2011, now Pat. No. 8,433,395, application No. 15/144,324, which is a continuation-in-part of application No. 13/931,228, filed on Jun. 28, 2013, now Pat. No. 9,339,202, which is a continuation-in-part of application No. 13/092,530, filed on Apr. 22, 2011, now Pat. No. 8,478,389, said application No. 13/931,228 is a continuation-in-part of application No. PCT/US2013/024770, filed on Feb. 5, 2013, and a continuation-in-part of application No. PCT/US2011/052371, filed on Sep. 20, 2011, application No. 15/144,324, which is a continuation-in-part of application No. 14/032,544, filed on Sep. 20, 2013, now Pat. No. 9,414,786, which is a continuation-in-part of application No. 13/293,632, filed on Nov. 10, 2011, now Pat. No. 8,543,195.

(60) Provisional application No. 62/155,253, filed on Apr. 30, 2015, provisional application No. 61/944,253, filed on Feb. 25, 2014, provisional application No. 61/257,718, filed on Nov. 3, 2009, provisional application No. 61/366,052, filed on Jul. 20, 2010, provisional application No. 61/359,462, filed on Jun. 29, 2010, provisional application No. 61/370,026, filed on Aug. 2, 2010, provisional application No. 61/555,165, filed on Nov. 3, 2011, provisional application No. 61/327,497, filed on Apr. 23, 2010, provisional application No. 61/412,108, filed on Nov. 10, 2010.

(51) Int. Cl.

| | | |
|---|---|---|
| *A61B 5/0456* | (2006.01) | |
| *A61B 5/0205* | (2006.01) | |
| *A61B 5/00* | (2006.01) | |
| *A61B 7/02* | (2006.01) | |
| *A61B 5/02* | (2006.01) | |
| *A61B 5/021* | (2006.01) | |
| *A61B 5/0245* | (2006.01) | |
| *A61B 5/026* | (2006.01) | |
| *A61B 5/0408* | (2006.01) | |
| *A61B 5/0452* | (2006.01) | |
| *A61B 5/046* | (2006.01) | |
| *A61B 5/0464* | (2006.01) | |
| *A61B 5/0468* | (2006.01) | |
| *A61B 5/0472* | (2006.01) | |
| *A61B 5/11* | (2006.01) | |
| *G06F 17/14* | (2006.01) | |
| *G06F 19/00* | (2011.01) | |
| *G06K 9/00* | (2006.01) | |
| *A61B 5/024* | (2006.01) | |

(52) U.S. Cl.
CPC .......... *A61B 5/0456* (2013.01); *A61B 5/0464* (2013.01); *A61B 5/0468* (2013.01); *A61B 5/0472* (2013.01); *A61B 5/04087* (2013.01); *A61B 5/1102* (2013.01); *A61B 5/7203* (2013.01); *A61B 5/7235* (2013.01); *A61B 7/02* (2013.01); *G06F 17/14* (2013.01); *G06F 19/3431* (2013.01); *G06K 9/0051* (2013.01); *G06K 9/0053* (2013.01); *A61B 5/024* (2013.01); *A61B 5/7253* (2013.01)

(56) References Cited

U.S. PATENT DOCUMENTS

| | | |
|---|---|---|
| 5,521,851 A | 5/1996 | Wei et al. |
| 5,776,073 A | 7/1998 | Garfield et al. |
| 5,792,065 A | 8/1998 | Xue et al. |
| 5,817,027 A | 10/1998 | Arand et al. |
| 5,827,195 A | 10/1998 | Lander |
| 5,987,352 A | 11/1999 | Klein et al. |
| 6,117,077 A | 9/2000 | Del Mar et al. |
| 6,389,308 B1 | 5/2002 | Shusterman |
| 6,589,189 B2 | 7/2003 | Meyerson et al. |
| 6,690,959 B2 | 2/2004 | Thompson |
| 6,701,170 B2 | 3/2004 | Stetson |
| 6,775,571 B1 | 8/2004 | Kroll |
| 6,822,564 B2 | 11/2004 | Al-Ali |
| 6,856,832 B1 | 2/2005 | Matsumura et al. |
| 7,096,060 B2 | 8/2006 | Arand et al. |
| 7,099,714 B2 | 8/2006 | Houben |
| 7,115,096 B2 | 10/2006 | Siejko et al. |
| 7,236,819 B2 | 6/2007 | Brockway et al. |
| 7,272,265 B2 | 9/2007 | Kouri et al. |
| 7,376,453 B1 | 5/2008 | Diab et al. |
| 7,480,529 B2 | 1/2009 | Li |
| 7,602,985 B2 | 10/2009 | Gao et al. |
| 7,627,369 B2 | 12/2009 | Hunt |
| 7,672,717 B1 | 3/2010 | Zikov et al. |
| 7,840,259 B2 | 11/2010 | Xue et al. |
| 7,846,104 B2 | 12/2010 | MacQuarrie et al. |
| 8,086,304 B2 | 12/2011 | Brockway et al. |
| 8,201,330 B1 | 6/2012 | Rood et al. |
| 8,214,007 B2 | 7/2012 | Baker et al. |
| 8,271,073 B2 | 9/2012 | Zhang et al. |
| 8,348,852 B2 | 1/2013 | Bauer et al. |
| 8,433,395 B1 | 4/2013 | Brockway et al. |
| 8,460,189 B2 | 6/2013 | Libbus et al. |
| 8,478,389 B1 | 7/2013 | Brockway et al. |
| 8,543,195 B1 | 9/2013 | Brockway et al. |
| 8,588,908 B2 | 11/2013 | Moorman et al. |
| 8,632,465 B1 | 1/2014 | Brockway |
| 8,755,876 B2 | 6/2014 | Chon et al. |
| 9,095,266 B1 | 8/2015 | Fu |
| 2003/0185408 A1 | 10/2003 | Causevic et al. |
| 2003/0236447 A1 | 12/2003 | Ritland |
| 2004/0138578 A1 | 7/2004 | Pineda et al. |
| 2005/0010120 A1 | 1/2005 | Jung et al. |
| 2005/0234361 A1 | 10/2005 | Holland |
| 2005/0265629 A1 | 12/2005 | Fu et al. |
| 2005/0283090 A1 | 12/2005 | Wells |
| 2006/0094992 A1 | 5/2006 | Imboden et al. |
| 2007/0219453 A1 | 9/2007 | Kremliovsky et al. |
| 2007/0219455 A1 | 9/2007 | Wong et al. |
| 2007/0260151 A1 | 11/2007 | Clifford |
| 2007/0265508 A1 | 11/2007 | Sheikhzadeh-Nadjar |
| 2008/0065158 A1 | 3/2008 | Ben-Ezra et al. |
| 2008/0097537 A1 | 4/2008 | Duann et al. |
| 2008/0183093 A1 | 7/2008 | Duann et al. |
| 2008/0200832 A1 | 8/2008 | Stone |
| 2008/0228094 A1 | 9/2008 | Audet et al. |
| 2008/0255464 A1 | 10/2008 | Vincent |
| 2009/0069703 A1 | 3/2009 | Takla et al. |
| 2009/0222262 A1 | 9/2009 | Kim et al. |
| 2010/0056940 A1 | 3/2010 | Moorman et al. |
| 2010/0063438 A1 | 3/2010 | Bengtsson |
| 2010/0234916 A1 | 9/2010 | Turcott et al. |
| 2011/0306895 A1 | 12/2011 | Nakashima et al. |
| 2012/0165691 A1 | 6/2012 | Ting et al. |
| 2012/0197144 A1 | 8/2012 | Christ et al. |
| 2012/0232417 A1 | 9/2012 | Zhang |
| 2013/0069768 A1 | 3/2013 | Madhyastha et al. |
| 2013/0109937 A1 | 5/2013 | Banet et al. |

(56) References Cited

U.S. PATENT DOCUMENTS

| | | |
|---|---|---|
| 2013/0289424 A1 | 10/2013 | Brockway et al. |
| 2014/0005988 A1 | 1/2014 | Brockway |
| 2014/0180597 A1* | 6/2014 | Brown ............... A61B 5/04012 |
| | | 702/19 |

OTHER PUBLICATIONS

H. Boudoulas, YH. Sohn, W. O'Neill, R. Brown, AM. Weissler. The QT greater that QS2 syndrome: a new mortality risk Indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic 1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution," Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J._Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvärinen, "New Approximations of Differential Entropy for Independent Component Analysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres- Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157-192 (1999).

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger AL et al. PhysioBank, PhysioToolkit, and PhysioNet: components of a new research resource for complex physiologic signals. Circulation 101(23): e215-e220, Jun. 13, 2000.

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression conference, pp. 523-541 (2000).

L. K. Saul and J. B. Allen, "Periodic component analysis: An eigenvalue method for representing periodic structure in speech," in NIPS, [Online]., pp. 807-813 (2000). Available: http://www.cs.cmu.edu/Groups/NIPS/00papers-pub-on-web/SaulAllen.pdf.

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, Mar. 2001.

M. Brennan, M. Palaniswami, and P. Kamen. Do Existing Measures of Poincare Plot Geometry Reflect Nonlinear eatures of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

(56) References Cited

OTHER PUBLICATIONS

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, p. 819-823 vol. 1.

M. Costa, A. L. Goldberger, and C.-K Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

Li, Cuiwei, Chongxun Zheng, and Changfeng Tai. "Detection of ECG characteristic points using wavelet transforms" Biomedical Engineering, IEEE Transactions on 42.1 (1995): 21-28.

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

O A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on Biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1 659-69.

Madalena Costa.et. al. Multiscale entropy analysis of biological signals. Physical Review E 71, 021906 s2005d.

M. Alghoniemy and A. Tewtik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

Inan, O.T.; Giovangrandi, L.; Kovacs, G.T.A.; Robust Neural-Network-Based Classification of Premature Ventricular contractions Using Wavelet Transform and Timing Interval Features , IEEE Transactions on Biomedical Engineering vol. 53 , Issue: 12 , , pp. 2507-2515.

L. Smith, A tutorial on Principal Components Analysis.

Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.

K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).

K. Todros and J. Tabrikian, "Blind Separation of Independent Sources Using Gaussian Mixture Model," IEEE Transactions on Signal Processing, vol. 55, No. 7, pp. 3645-3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

X. Li, X. Yao, J. Fox, and J. Jefferys "Interaction Dynamics of Neuronal Oscillations Analysed Using Wavelet Transforms," Journal of Neuroscience Methods 160, pp. 178-185 (2007).

R Schimpf, Ch Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008 ; 5(2): 241-245.

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and full-band electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14 , Issue: 2, pp. 152-159.

Dash S, Chon KH, Lu S, Raeder EA. Automatic real time detection of atrial fibrillation. Ann Biomed Eng. Sep. 2009;37(9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

(56) References Cited

OTHER PUBLICATIONS

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the VALIANT trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S.Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg.

http://www.physionet.org/physiobank/database/mitdb/.

Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

Kellermann, et al.,"A mobile phone based alarm system for supervising vital parameters in free moving rats," BMC Research Notes 2012, 5:119, Feb. 23, 2012.

http://www.simplehelp.net/2006/09/12/how-to-set-up-outlook-2003-for-email/.

Lee, J., "Time-Varying Coherence Function for Atrial Fibrillation Detection". IEEE Transactions on Miomedical Engineering vol. 60, No. 10, Oct. 2013.

C. Li, C. Zheng, and C. Tai, "Detection of ECG characteristic points using wavelet transforms," IEEE Trans. Biomed. Eng., vol. 42, pp. 21-28, 1995.

V.X. Afonso, W.J. Tompkins, T.Q. Nguyen, and S. Luo, "ECG beat detection using filter banks," IEEE Trans. Biomed. Eng., vol. 46, pp. 192-202, 1999.

Z. Dokur, T. Olmez, E Yazgan, and O.K. Ersoy, "Detection of ECG waveforms by neural networks," Med. Eng. Phys., vol. 19, No. 8, pp. 738-741, 1997.

Paul S Addison. Wavelet transforms and the ECG: a review. Physiol. Meas. 26 (2005) R155-R199.

JS. Sahambi', S.N. Tandonz5 R.K.P. Bhatt. Using Wavelet Transforms for ECG Characterization. IEEE Engineering in Medicine and Biology, Jan./Feb. 1997.

Beck et al., "An Inventory for Measuring Depression", Arch Gen Psychiatry, 4:561-571 (Jun. 1961).

Galinier et al., "Depressed low frequency power of heart rate variability as an independent predictor of sudden death in chronic heart failure", Eur. Hrt. J., 21:475-482. (2000).

Ghasemi et al., "A Semi-Automated QT Interval Measurement Based on Wavelet and Energy Analysis," http://physionet.org/challenge/2006/papers.

Pincus, "Approximate entropy as a measure of system complexity", Proc Natl Acad Sci USA, 88:2297-2301 (Mar. 1991).

Quintana et al., "Considerations in the assessment of heart rate variability in biobehavioral research", Frontiers in Physiology, 5(Art. 805):1-10 (Jul. 22, 2014).

SadAbadi et al., "A mathematical algorithm for ECG signal denoising using window analysis," Biomed Pap Med Fac Univ Palacky Olomouc Czech Repub. Jun. 2007;151(1):73-8.

Woo et al., "Patterns of beat-to-beat heart rate variability in advanced heart failure", Am Heart J., 123:704-710 (Apr. 1992).

\* cited by examiner

METHOD AND APPARATUS FOR ASSESSING CARDIAC AND/OR MENTAL HEALTH

FIELD

Various aspects of the present invention relate to the processing of ECG and other signals indicative of the activity of a beating heart, and more particularly, aspects relating to providing diagnostic indicators of central mediated neurological disorder (e.g. anorexia and clinical depression), degree of mental stress, cardiac ischemia, and heart failure decompensation prediction.

BACKGROUND

The present invention will be useful for evaluating and detecting pathologies that impact mental and cardiac health. It is known that vagal influence on the heart rate is reduced during a depressive state and that beat-to-beat (btb) dynamics and vagal balance are in-turn influenced by cardiac function.

A quantitative assessment of depressive state has application in clinical trials and in management of depressive disorder. Current means of assessing depressive state involve the use of questionnaires such as the Beck Depression Inventory [1]. Subjectivity of responses often leads to a high degree of error in measured result vs. actual clinical effect. No technique is currently available that can provide a reliable quantitative assessment of depressive state.

Assessment of cardiac ischemia, including myocardial infarction (MI), is important in clinical research and clinical care. Current means of assessing cardiac ischemia include the use of a 12 lead ECG to measure ST segment elevation. This test is performed under both stressed and unstressed conditions in the clinic. Ischemia and MI, however, are often transient and are triggered by mental stress and other stimuli as the patient goes about their normal every day activities. It therefore can be useful to assess ischemia and MI on ambulatory patients as they go about their normal activities.

Measurement of ST segment elevation is sometimes performed on continuous ECG recordings (i.e. Holter) to non-invasively assess ischemia in ambulatory patients, but noise and artifact render accurate measurements difficult. There is no technique available that provides an accurate non-invasive assessment of cardiac ischemia or detection of MI in ambulatory subjects.

Prediction and detection of heart failure decompensation is useful in medical management of patients with heart failure as detection can prompt care providers to intervene early and prevent hospitalization. Current non-invasive techniques to assess heart failure decompensation in ambulatory patients include daily measurement of weight and patient self-assessment. Sensitivity and specificity of existing techniques is poor and hence the rate of avoidable hospitalizations is excessive.

SUMMARY

Various aspects of the present invention are directed to devices, computer implemented methods, and systems for assessing mental status, assessing cardiac ischemia, detection of MI, and detecting heart failure decompensation evaluating beat-to-beat (btb) QT, TQ and RR interval dynamics in a manner that addresses the challenges and limitations of existing methods.

In accordance with various example embodiments, the peak of each R-wave is detected in the ECG and a sequence of interbeat RR intervals is computed. In some embodiments Q-onset, and T-offset are also detected and a sequence of beat-to-beat QT intervals is also computed. Each sequence of computed intervals is cleaned and any gaps that result from the cleaning process are interpolated. In one aspect of this invention, intervals to be excluded are those that were detected in error, were excessively noisy and hence of suspect accuracy, or were part of ventricular arrhythmia.

In one embodiment, the cleaned and interpolated sequence of RR intervals is decomposed into subcomponents and the energy in the resulting scales is compared to assess mental health, stress level, and/or centrally mediated neurological disorder (CMND) such as depression or anorexia. In one embodiment the time course profile of energy in the scales is compared. In another embodiment, the periodicity of the energy level in one or more scales is evaluated. In another embodiment, the degree of randomness of one or more scales is evaluated. In yet another embodiment, the circadian variation of the energy contained in one or more scales is evaluated. In yet another embodiment, the energy contained in one or more scales during sleep and awake is compared. In yet another embodiment, two or more of these metrics are combined into a single metric indicative of CMND. In another embodiment, the cleaned and interpolated sequence of QT intervals is decomposed into subcomponents and the resulting scales evaluated using the same techniques as are used for RR intervals.

In another embodiment, TQ is computed using a cleaned sequence of btb QT and RR values. In one aspect of this invention, restitution is evaluated using the QT/TQ vs. RR distribution to assess cardiac risk. In one embodiment, cardiac risk is assessed by evaluating the change in QT/TQ for a change in RR.

In another embodiment, a Poincare plot is computed from a cleaned sequence of QT intervals and the spatial characteristics of the plot are evaluated.

Clustering at various locations on the plot is indicative of alteration in autonomic tone. In one aspect of this invention the location and distribution of clusters is evaluated by examining the pattern in which beats chronologically populate each cluster as well as define the area in and between such clusters to be related to observed clinical outcomes during the same collection period.

BRIEF DESCRIPTION OF DRAWINGS

The invention may be more completely understood in consideration of the following detailed description of various embodiments of the invention in connection with the accompanying drawings, in which.

Figure 1:
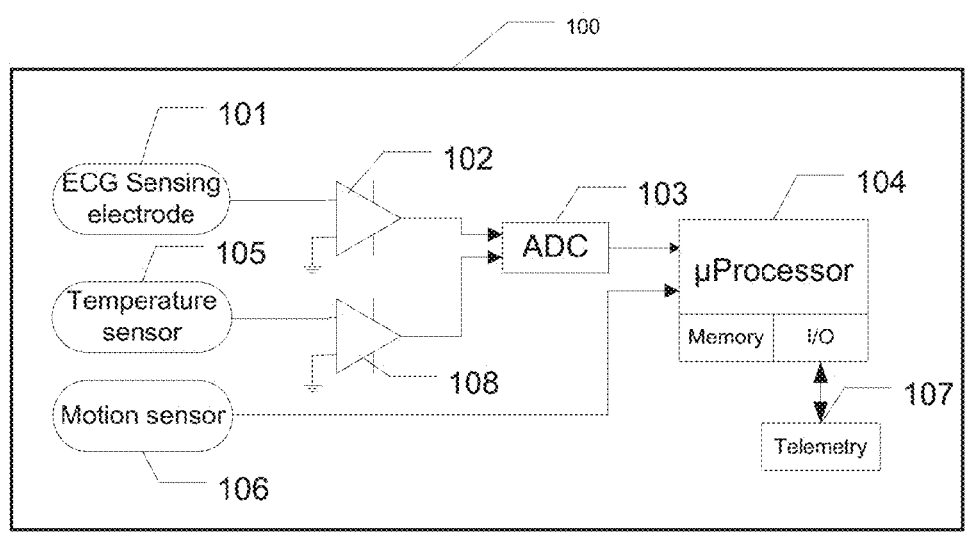
FIG. 1 illustrates an apparatus for sensing, measuring and processing signals for assessing mental status and cardiac risk.

While the invention is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

Various example embodiments of the present disclosure relate to circuits, computer implemented software, devices, and systems that acquire and process cardiac-related signals (e.g. ECG) for the purpose of evaluating CMND, heart failure decompensation prediction, myocardial infarction, and cardiac ischemia. While the present disclosure is not necessarily limited to this application, various aspects of the disclosure may be appreciated through a discussion of examples using this context.

As discussed above, there is no quantitative means of assessing CMND. Further, there is no accurate means available to non-invasively detecting cardiac ischemia nor to predict heart failure decompensation in ambulatory patients. Implementation of circuits, computer implemented software, devices, and systems capable of addressing this unmet need is a significant challenge. Accordingly, various aspects of the present invention are directed to addressing this challenge.

As may be implemented in accordance with one or more embodiments, a time series of cardiac intervals (e.g., RR or QT intervals) is computed from a recording of activity of a beating heart of a subject, and the time series is decomposed into subcomponents. An envelope of at least one of the subcomponents is computed, and the presence of a depressive mental state of the subject is detected based upon characteristics of the envelope.

The presence of the depressive state can be detected using a variety of approaches. For instance, such a state may be detected based on the presence of one or more of a periodic component of a predetermined frequency, a time averaged mean energy in a first scale that exceeds a time averaged mean energy in a second scale for a specified time, and increased entropy in one of the subcomponents corresponding to a high frequency band. In some embodiments, the depressive state is detected based on a degree of randomness of fluctuations in energy of the time series over a predetermined time period (e.g., by computing entropy and/or using sample entropy and approximate entropy).

In various embodiments, the time series of inter-beat intervals is computed as follows. A plethora of heart beats are detected in the recording, a raw sequence of inter-beat intervals is computed from consecutive ones of the detected beats, and invalid beats are identified from the detected beats. A cleaned sequence of inter-beat intervals is generated by excluding intervals computed using ones of the beats identified as being invalid, and the cleaned sequence of inter-beat intervals is resampled to create an equispaced time series of inter-beat intervals. The invalid beats may be identified based on, for example, characteristics in the recording selected from the group of ventricular arrhythmias, atrial fibrillation, characteristics indicating that a signal detected as a beat is not a beat, and noise beyond a noise threshold.

In some embodiments, invalid beats are identified by detecting ectopic beats as follows. The recording is decomposed into subcomponents, the presence of ventricular depolarizations is detected in the subcomponents, and a window is established around each detected ventricular depolarization. The energy of high frequency and low-frequency subcomponents in each window is computed. For each window, the ratio of low frequency energy to high frequency energy is computed and used to detect the presence of an ectopic beat in the window. Computing high frequency energy in the window may include, for example, selecting one or more subcomponents corresponding to high frequency and computing the high frequency energy using at least one of the sum of squares of the amplitude and the sum of the absolute values of the amplitude.

A variety of other characteristics may be detected and utilized in evaluating the subject. In various embodiments, the presence of a CMND state is detected based on characteristics of an envelope as above and temperature of the subject. The temperature can thus be measured or otherwise obtained.

In other embodiments, the presence of a depressive mental state is detected by evaluating characteristics of the motor activity measurements (which can be provided or actively obtained).

Referring to FIG. 1, which provides a block diagram of device 100, an ECG signal is captured via sensing electrode (or electrodes) 101, is amplified with amplifier 102, digitized with ADC 103, and the digitized signal is processed using a computerized algorithm implemented in computing device 104. In one embodiment, a body-worn device acquires and processes the ECG signal to extract information to assess the patient's mental and/or cardiac status. In other embodiments, the ECG signal is recorded by a body worn device and is post-processed to extract the desired information from the ECG for the assessment. It should be recognized that signals other than ECG can be captured by sensing electrode 101. In other embodiments, a photoplethysmography signal obtained from the tissue is used.

In some embodiments the device also includes temperature sensor 105. In one embodiment, temperature sensor 105 can be a YSI (Yellow Springs, OH) series 400 thermistor probe for measuring surface (skin) or rectal temperature. In some embodiments, it is useful to place a layer of adhesive-backed foam over the probe as an insulator when measuring skin temperature so that the measured temperature is more indicative of core body temperature. Temperature measurements can be useful for quantifying the circadian rhythm pattern of a subject and, when the probe is placed on an extremity, can also be useful for providing an indicator of peripheral circulation. Quantifying the circadian rhythm of the patient can provide an indication of CMND as these pathologies are often associated with a biological rhythm disturbance [2]. When combined with other metrics, knowledge of circadian characteristics could improve the accuracy of the assessment.

In some embodiments the device also includes motion sensor 106. In one embodiment, motion sensor 106 is a triaxial accelerometer such as the Analog Devices (Norwood, Mass.) ADXL335. Motion sensor 106 can be used to determine whether the patient is physically active or sedentary. Knowing if the subject is physically active can be useful for qualifying beat-to-beat measurements as physical activity can mask changes in autonomic tone that may be indicative of a pathology. In other scenarios, it may be helpful to limit the assessment to time periods when the heart is under stress as indicated by period of high levels of physical activity. For example, if the physical activity associated with brisk walking at a certain rate was defined then measurements of btb ECG activity could be determined within a prespecified range for comparison to determine improvements or impairments of cardiac function. In another embodiment the sensor can be used to determine the sleep state. In one embodiment, the time of sleep can be used to characterize changes in HRV metrics.

Figure 2:
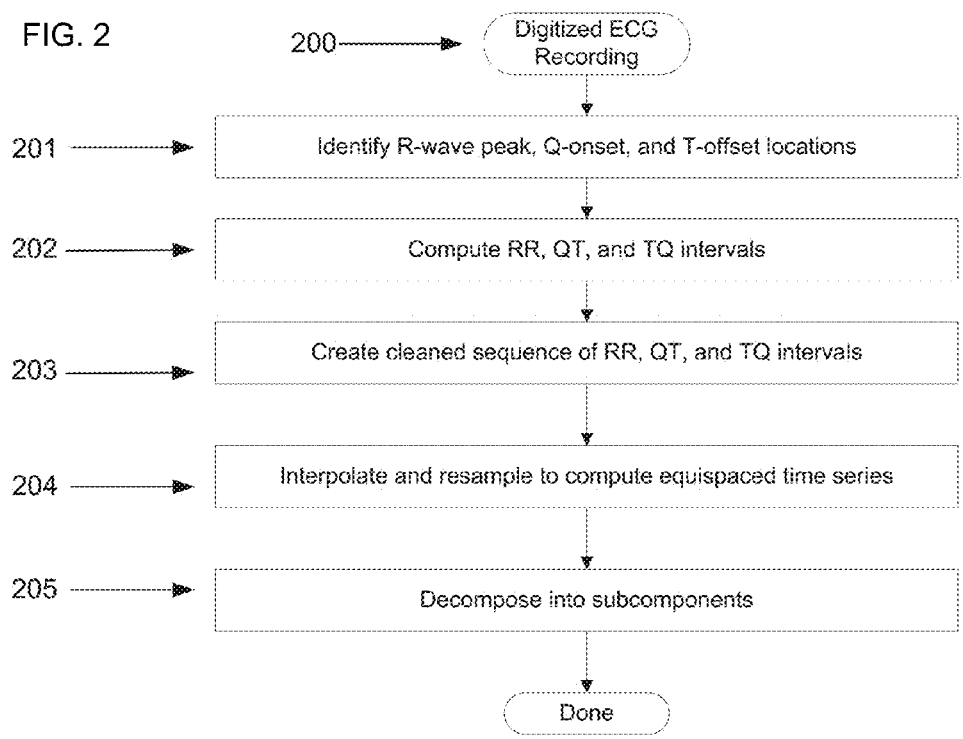
FIG. 2 illustrates the initial steps used to process the ECG to prepare for computing metrics of mental status and cardiac risk.

In one embodiment beat-to-beat measurements of one or more of RR, QT, and TQ intervals are obtained from an ECG signal. Referring to FIG. 2, fiducial marks for Q-onset, R-wave peak, and T-wave offset are detected for as many cardiac cycles as possible in step 201. In one embodiment these fiducial marks are detected using techniques described in U.S. Pat. Nos. 8,632,465 and 8,433,395 and PCT application PCT/US13/24770 which are included herein by reference. Alternately, fiducial marks are detected using techniques described in [5].

In various embodiments, QT interval (time from Q-onset to T-offset of the current beat), RR interval (time between the R-wave peak of the prior beat and the current beat), and TQ interval (time from T-offset to Q-onset) are computed in step 202. In some embodiments, TQ interval is computed as difference between prior RR interval and current QT interval. In some embodiments, it is useful to create a cleaned sequence for an interval measurement as in step 203. Cleaning removes interval measurements that are inaccurate or suspected as being inaccurate in order to avoid compromising the integrity of the computed metrics. Cleaning can be accomplished by identifying QRS complexes that were falsely triggered by noise in the ECG recording or are associated with arrhythmias (e.g. atrial fibrillation, ventricular ectopy, ventricular tachycardia). If a QRS complex is identified as falsely triggered, the QT, TQ, and RR intervals associated with that cardiac cycle are ignored in subsequent analysis. Likewise, if there is excessive noise surrounding a Q-onset or T-offset, they are ignored in subsequent analysis. In some embodiments, identification of a T-offset that is potentially in error is identified using techniques described in U.S. Pat. No. 8,433,395. In one embodiment, identifying QRS complexes that are associated with arrhythmias is accomplished using techniques described in U.S. patent application 61/944,253 which is herein included in its entirety by reference.

Metrics Derived from RR Intervals

Figure 3A:
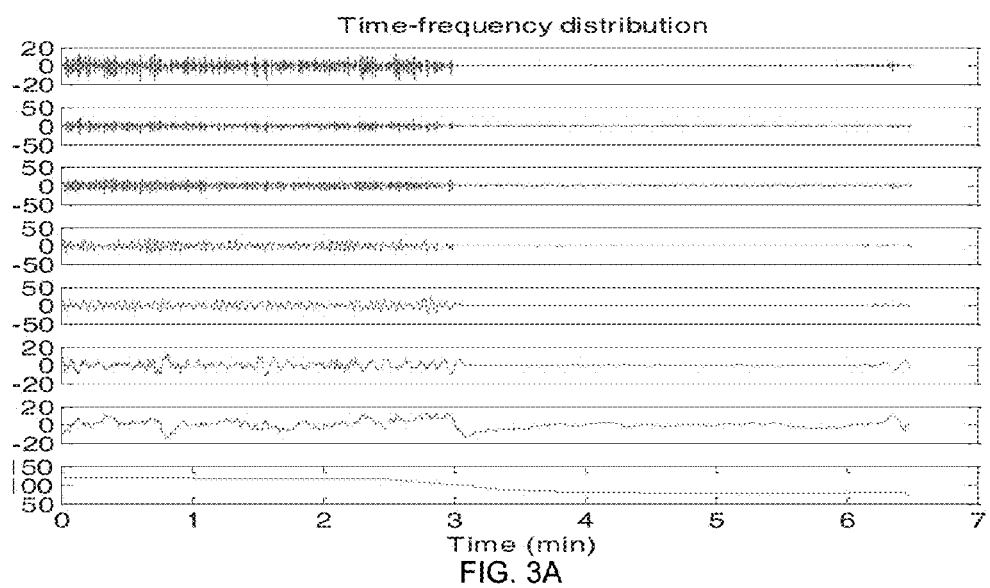
FIG. 3A provides an example of a time series of subcomponents derived from an ECG recording.
Figure 3B:
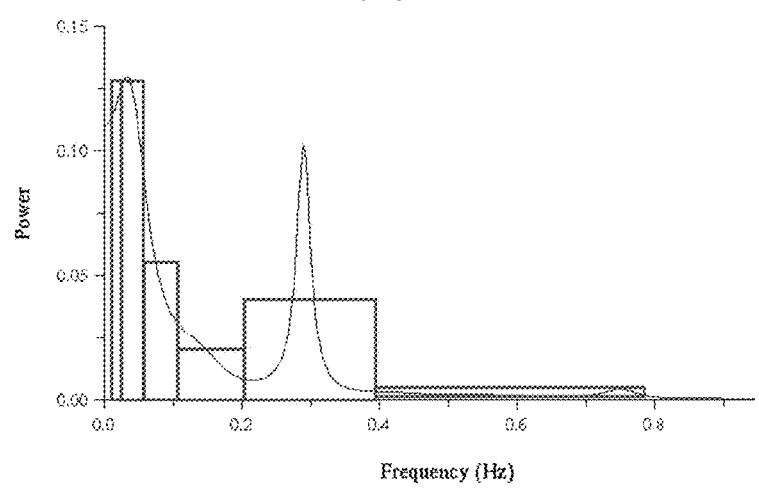
FIG. 3B illustrates the correspondence between power spectrum and energy of subcomponents.

In one embodiment, a cleaned sequence of RR intervals is interpolated and is decomposed into subcomponents (also sometimes referred to as scales) as in steps 204 and 205. In another embodiment, a cleaned sequence of QT intervals is interpolated and is decomposed into subcomponents. In some embodiments, various characteristics of the resulting subcomponents computed from RR and/or QT intervals are evaluated to assess stress, CMND, and cardiac risk. An example time series of subcomponents is shown in FIGS. 3A and 3B. Referring to FIG. 3A, each subcomponent (also referred to as a scale) corresponds to a frequency band FIG. 3B in the power spectral density plot. The variance of individual subcomponents approximates the power in the corresponding frequency band.

In another embodiment, metrics derived from the subcomponents are used to assess the cardiac risk. In one embodiment, a reduction in energy of the scale corresponding to a low frequency band (e.g. 0.04-0.15 Hz, for humans) would indicate a worsening of cardiac status and trigger additional observation of the patient or testing to determine the cause and effect treatment. An indication of worsening condition could indicate the presence of ischemia, increased risk of arrhythmias, or onset of heart failure decompensation. This could lead to early intervention to, for example, prevent hospitalization.

In one embodiment, an envelope is computed for each subcomponent time series, the envelope representing the energy contained in the subcomponent. The envelope is computed in a manner that preserves all variations contained in the subcomponent. In one embodiment, the energy in two or more scales is compared to compute a metric of mental status, stress level, and/or CMND. In one embodiment, energy in two or more scales is compared to provide a metric of relative energy change. In one embodiment the scales corresponding to low frequency and high frequency are compared. The relative increase of energy in higher frequency bands (0.15-0.4 Hz in humans) is an indicator of more erratic heart rate and respiratory patterns. In one embodiment motion sensor 106 provides a measure of patient activity that is used to detect sleep. It may be useful to evaluate the energy in the higher frequency bands during sleep for the purpose of detecting heart failure decompensation [6].

In another embodiment the time course profile of energy in one or more scales is compared. In one embodiment, the time course profile is evaluated by quantifying periodicities in the energy contained in one or more scales. Periodicities of interest range from a few minutes to about 24 hours. In one embodiment, the subcomponents derived from RR and/or QT intervals are examined for the presence of specific periodicities such as those related to respiration cycle, rapid eye movements during sleep and circadian periodicities. In one embodiment, periodicities are evaluated using autocorrelation.

In another embodiment, the energy contained in one or more scales during sleep and awake are compared.

In another embodiment, one or more scales are evaluated to determine whether the changes in energy in one or more scales is periodic or random. For the purpose of explanation, this embodiment is referred to hereinafter as using a metric of randomness of the one or more scales to evaluate mental status, stress level, and/or CMND state. In one embodiment randomness is evaluated by computing a measure of sample entropy SE(t). In some embodiments, SE(t) is computed using sample entropy as in Richman J S, Randall M J, "Physiological time-series analysis using approximate entropy and sample entropy," Am J Physiol Heart Circ Physiol 278:H2039-H2049 (2000), which is fully incorporated herein by reference. In another embodiment SE(t) is computed using approximate entropy, such as in Pincus S M, "Approximate entropy as a measure of system complexity," Proc Natl Acad Sci USA 88:2297-2301 (1991), which is fully incorporated herein by reference. In other embodiments one or more of detrended fluctuation analysis (DFA), correlation dimension, largest Lyapunov exponent, fractal dimension, Hurst exponent, and recurrence plots are used as metrics of regularity or complexity. DFA quantifies the extent of short and long-range correlations in a time series, via a metric called a scaling exponent. In one embodiment, the fluctuations of a detrended integrated time RR time series are calculated as root mean square values F(n) of individual subcomponents SUBn(t)s. The scaling exponent is then approximated as a slope a of the linear fit in the log-log plot: log F(n)=α log n. When scaling exponent a is approximately 0.5, the time series dynamic is similar to white noise (highly random).

In one embodiment, two or more of these metrics are combined into a single metric indicative of the mental health, stress level, and/or CMND state. In another embodiment, the cleaned and interpolated sequence of QT intervals is decomposed into subcomponents and the resulting scales evaluated using the same techniques as are used for RR intervals.

In one embodiment, device 100 in FIG. 1 incorporates motion sensor 106. In one embodiment, motion sensor 106 is a triaxial accelerometer. Measurements from motion sensor 106 are used to assess whether the subject is active or still. In some embodiments, the degree of physical activity is assessed using information from the accelerometer. Changes in physical activity often correlate to a change in the distribution of energy in the subcomponents computed in step 205. In some embodiments, the degree of physical activity is used to qualify use of the diagnostic information derived from the ECG. Measurements from motion sensor 106, for example, can be used to determine if the patient is highly active, moderately active, or at rest. Computing a diagnostic metric only when physical activity is within a prespecified range provides for standardization of the circumstances under which the metric is computed and may be useful when comparing metrics obtained at different time points. In one embodiment, CMND and mental status is only evaluated and provided for diagnostic purposes when the patient is at rest. In another embodiment, metrics derived from the QT/TQ vs. RR distribution are used to assess cardiac risk only when the degree of physical activity is within a predefined range. This would allow a standard measure for comparison between subjects and within subjects, for example, over the course of a particular therapy to assess the progression of the patient's clinical status. In other embodiments, physical activity is characterized by the level of muscle noise present in the raw ECG recording. In another embodiment, motion sensor 106 and muscle noise are used to assess the level of physical activity. In one embodiment, muscle noise is measured using techniques described in U.S. Pat. No. 8,632,465.

Metrics Derived from Btb QT, TQ and RR Measurements Using TQ Vs. RR Loops

In another embodiment, the TQ vs. RR loops are computed as a diagnostic metric from a cleaned sequence of btb TQ and RR pairs to assess cardiac risk (e.g. ischemia, and heart failure decompensation and detection of myocardial infarction). In one embodiment, the area of sequential TQ vs. RR loops is computed to assess the degree of hysteresis and the resulting measurement of area is compared to a threshold. In one embodiment one or more loops are computing using consecutive TQ/RR pairs during a time period where RR decreases (increase in heart rate) by more than a predetermined amount. In some embodiments, the time period for which a loop is computed is determined by the duration of time required for the RR interval to stabilize following the disturbance. In one embodiment, loop area is computed by fitting an ellipse to one or more TQ vs. RR loops and computing the area of the best-fitting ellipse according to the formula:

$$\text{Area} = Pi * A * B, \text{ where } A, B = \text{axes}/2 \qquad \text{Formula 1}$$

and comparing the area of the elipse to a threshold. A larger area is indicative of greater hysteresis and greater cardiac risk. In one embodiment, shape is evaluated by computing a ratio of length of the shape in the X-axis over the length in the direction of the Y-axis. In another embodiment, the shape is quantified using a ratio of the major and minor axes of the ellipse.

In some embodiments, a diagnostic metric based upon TQ vs. RR loops is computed when RR is a specified range (e.g. 400 to 1000 msec for adult human beings). In other embodiments, a diagnostic metric based upon TQ vs. RR loops is computed when measurements obtained from motion sensor 106 indicate that activity of the patient exceeds a threshold for a prespecified time span. For example, a diagnostic metric based upon TQ vs. RR loops is computed only when motion sensor 106 indicates that the patient is at least moderately active. In some embodiments, TQ vs. RR loops are evaluated when patient activity is increasing or decreasing by greater than a predetermined amount. Increasing or decreasing activity provides for a condition where heart rate is increasing or decreasing. During this time, the likelihood of heterogeneity in heart rhythm is greater, allowing the TQ vs. RR loops to detect abnormal hysteresis.

In one embodiment, the area of one or more loops is computed. In some embodiments, if more than one loop is evaluated, the mean area is computed and the resulting mean is compared to a threshold Th-TQ/RRloop. If the mean is larger than threshold Th-TQ/RRloop, then the subject's restitution is impaired and the patient may have an increased cardiac risk. In one embodiment Th-TQ/RRloop is established based upon measurements obtained from normal and diseased age-matched populations. In another embodiment, Th-TQ/RRloop is individualized for patients suffering from cardiac disease using a baseline recording obtained when the patient is diagnosed as healthy by their physician, or as stabilized after a heart failure exacerbation. Th-TQ/RRloop is established by adding a margin of error to the value measurement when healthy. In one embodiment, measurements at a timepoint are compared to Th-TQ/RRloop during periods of inactivity as characterized by motion sensor 106. In one embodiment metrics are computed using one or more TQ vs. RR loops obtained during a predetermined physiologic challenge. In one embodiment, the physiologic challenge coincides with the changes invoking baroreflex control such as premature ventricular beat. In another embodiment, the start of physiologic challenge coincides with an increase in heart rate of about 20 bpm and lasting for >10 seconds.

Metrics Derived from btb RR, QT and TQ

In another embodiment beat-to-beat (btb) data derived from ECG is used to compute a metric of cardiac risk. This metric can indicate one or more of ischemia and heart failure decompensation.

Figure 4:
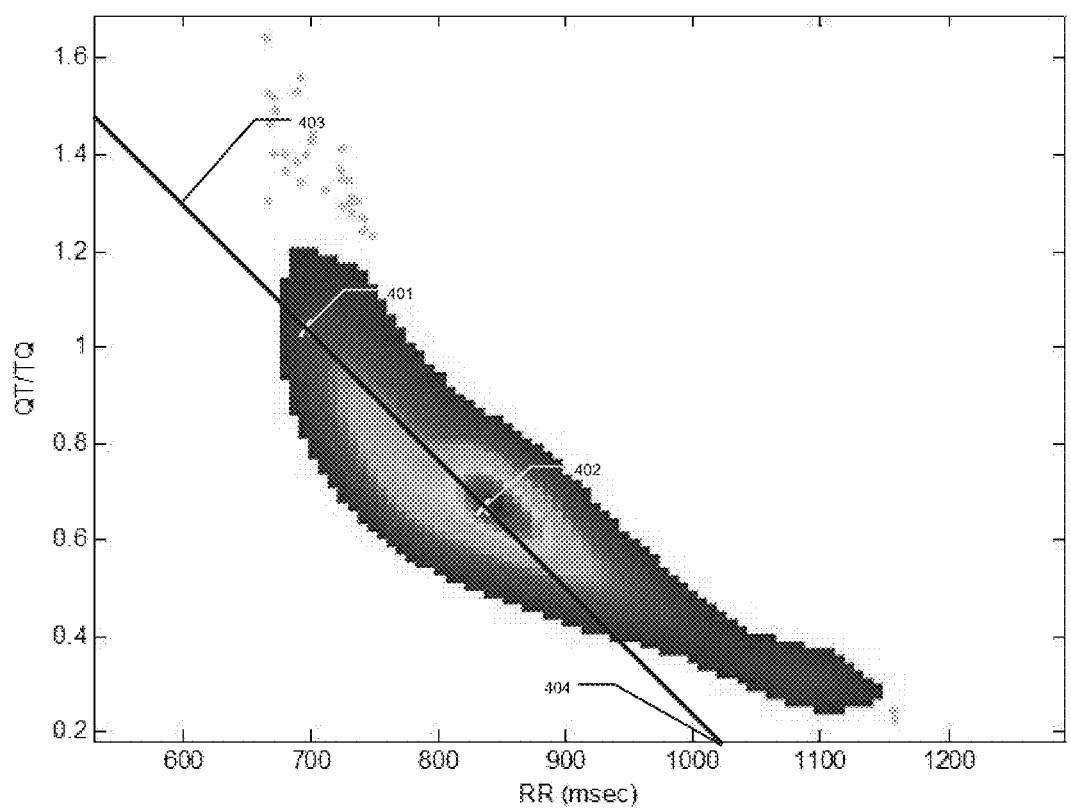
FIG. 4 provide an example QT/TQ vs. RR distribution where a subject is at very low cardiac risk.

In one embodiment a metric of cardiac risk is computed from the cleaned sequence of btb TQ, QT, and RR values. Referring to FIG. 4, the ratio of the cleaned QT/TQ values is plotted vs. RR of the previous cardiac cycle for a specified time period. In one embodiment the time period is 24 hours, but in other embodiments the time period from which the plot is generated ranges from 1 hour to 48 hours.

In one embodiment two statistical points of the cloud plot are identified and the slope and intercept of a line spanning these two points are calculated. In one embodiment, first point 402 is the median of the QT/TQ values on y-axis and median of RR values in x-axis (402). In another embodiment first point 402 is found as median RR value at which QT/TQ are equal to preset value Th6. In one embodiment the Th6 is about one. In another embodiment the first point 402 is found as the median QT/TQ value at a predetermined RR interval, such as 850 msec.

In one embodiment, second point 401 is computed as upper confidence limit of QT/TQ values and the median of the corresponding RR values. In another embodiment, second point 401 is computed as the upper confidence limit of QT/TQ values and the lower confidence limit of RR values. In one embodiment, the upper confidence limit of QT/TQ values is computed as the 97.5 percentile of the QT/TQ distribution. In other embodiments, the upper confidence limit is computed as a percentile of the QT/TQ distribution range from 95% to 99.5%. In one embodiment, the lower confidence limit of RR values is computed as the 2.5 percentile of the RR distribution.

Figure 5:
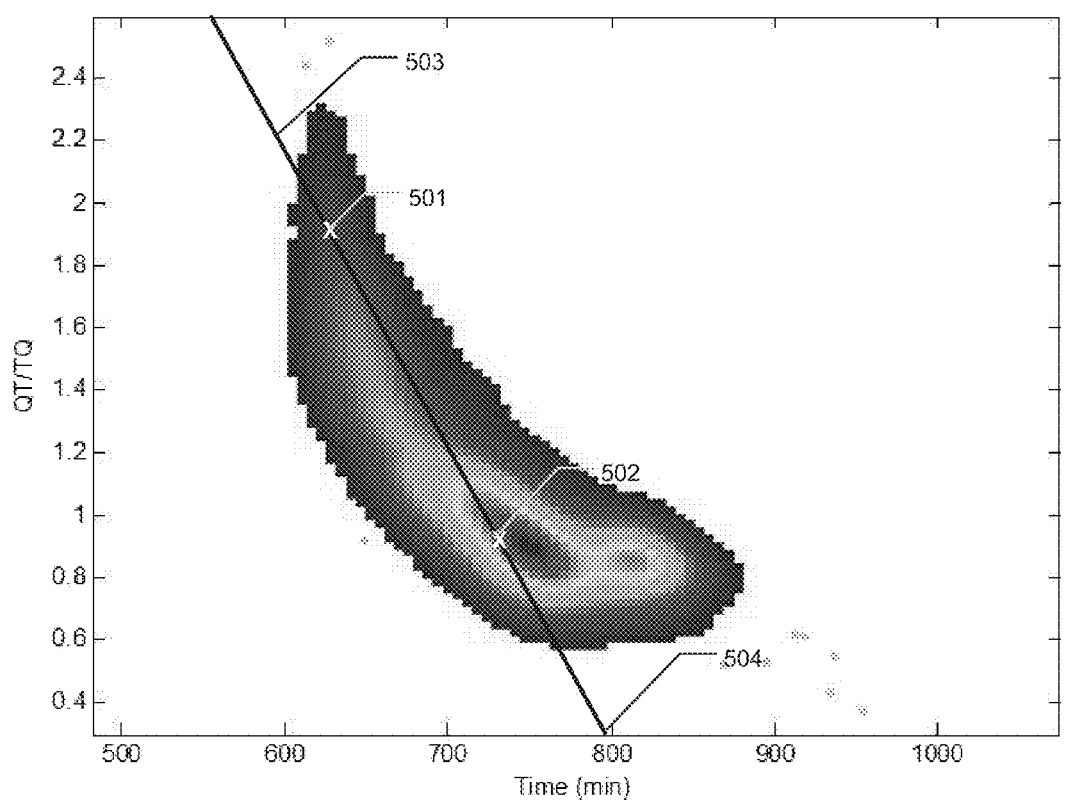
FIG. 5 provides an example QT/TQ vs. RR distribution where a subject is at high cardiac risk.

In one embodiment, line 403 is fit to these two points and its slope ($\Delta Y/\Delta X$) and X-axis intercept are identified. The X-axis slope is referred to as the Fossa slope. The Fossa slope of line 403 is computed and compared to a threshold to determine the degree of cardiac risk. If the absolute value of the Fossa slope |slope|>Th4, the cardiac risk is high. If between Th4 and Th5, then the risk is moderate. If less than Th5, the cardiac risk is low. High cardiac risk may indicate presence of an ischemic event, impending heart failure decompensation, or an increasing risk of an arrhythmic event or myocardial infarction. FIG. 5 provides an example where the |slope|>Th4, indicating the subject is at high cardiac risk. FIG. 4 provides an example where the |slope| of line 403 is <Th5 and cardiac risk is low.

In some embodiments, threshold values are established empirically and in some embodiments may vary from patient to patient. In other embodiments, threshold values are obtained from a normal age-match population of patients with varying degrees of cardiac risk. Th4 is determined based upon measurements obtained from patients diagnosed as having high cardiac risk and Th5 is diagnosed for patients diagnosed as having low cardiac risk. In one embodiment, a baseline measurement may be obtained when the patient's condition is stable and is in reasonably good health. The Fossa slope is computed and Th5 is established as 125% of the baseline 'slope' and Th4 is established as 200% of the baseline |slope|. If |slope| exceeds Th5 the care provider may elect to examine the patient and/or intervene to avoid a worsening condition. Based upon the results of the patient's examination during this condition of elevated cardiac risk, Th5 and Th4 may be adjusted to better represent appropriate thresholds for the patient. In one embodiment, slope is calculated as the absolute value of $\Delta(QT/TQ)/\Delta RR$ (seconds) and Th 4 is about 8 and Th5 is about 4.

In some embodiments the X-axis intercept 404 of line 403 is identified. Intercept 404 is compared to thresholds Th2 and Th3. If intercept 404 is above Th2, the cardiac risk is low. If between Th2 and Th3, then it is moderate. If less than Th3, the cardiac risk is high.

High cardiac risk may indicate presence of an ischemic event, myocardial infarction, impending heart failure decompensation, or an increasing risk of an arrhythmic event. Differentiation of the type of risk encountered is established based upon patient history and current symptoms. FIG. 5 provides an example recording where RR intercept is <Th3, indicating the subject is at high cardiac risk. Note that RR at intercept 504 is about 800 vs. 1020 for intercept 404. Threshold values are set empirically and may vary from patient to patient.

Figure 8:
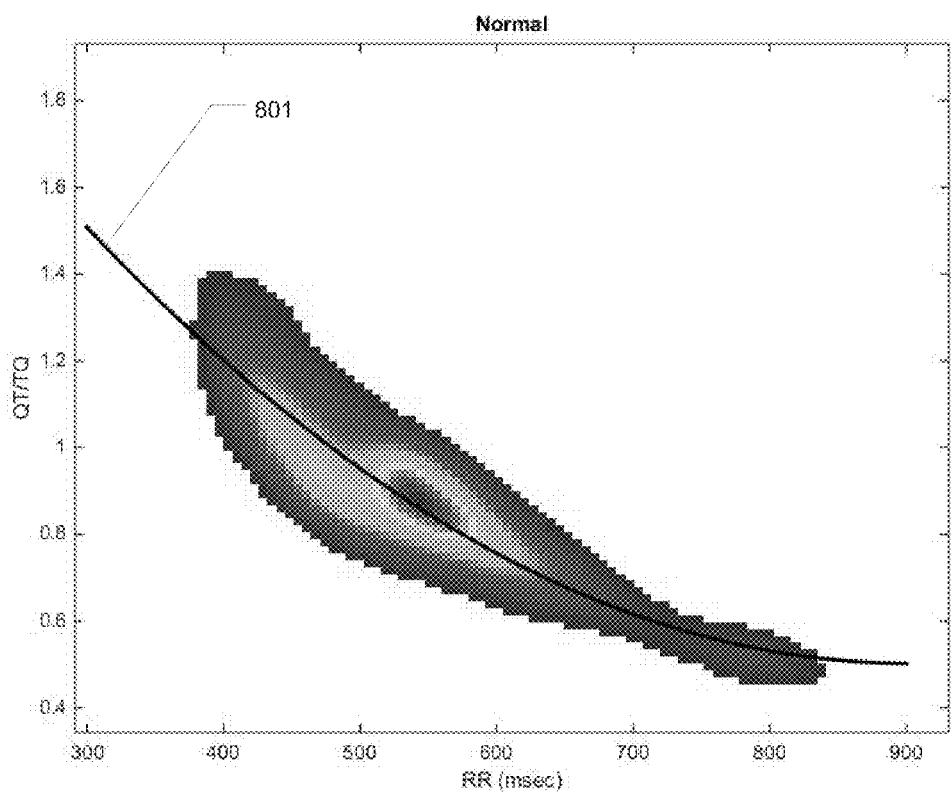
FIG. 8 provides an example of QT/TQ vs. RR with non-linear curve fit indicating low cardiac risk.
Figure 9:
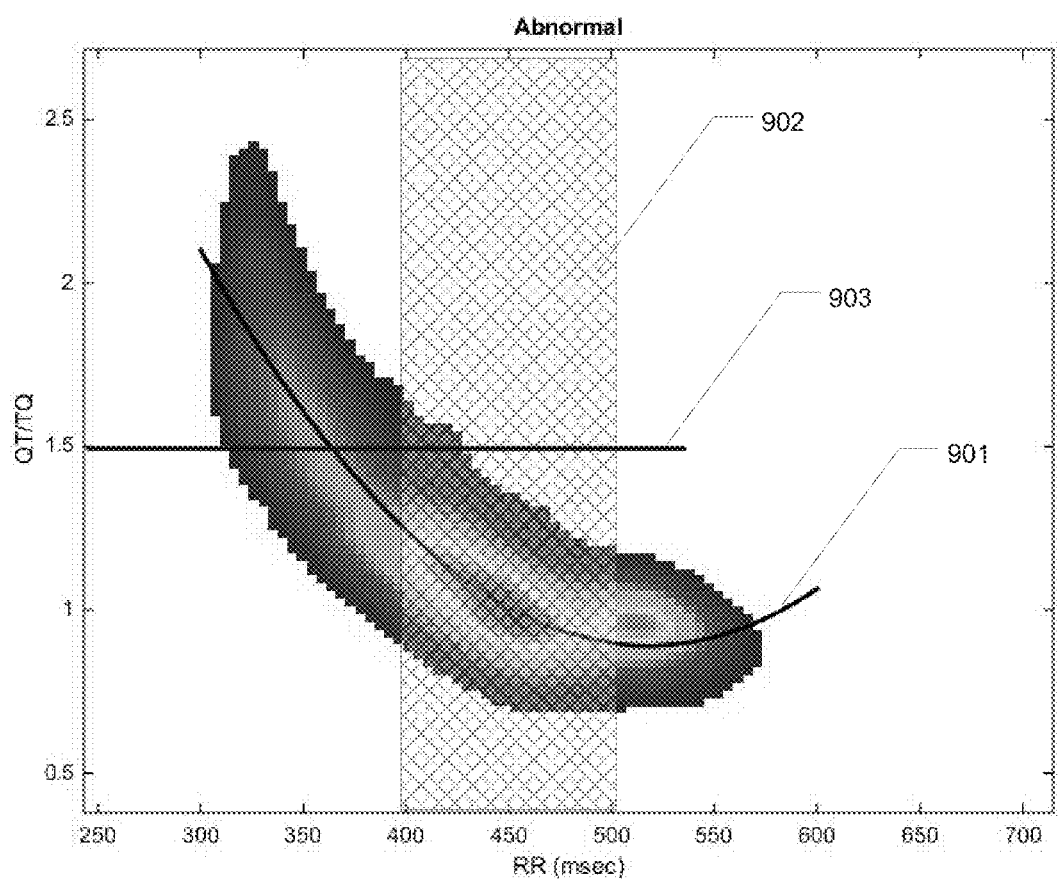
FIG. 9 provides an example of QT/TQ vs. RR with a non-linear curve fit potentially indicating a high cardiac risk.

FIG. 8 represents a QT/TQ vs. RR distribution for a subject with low cardiac risk (including fitted non-linear function 801) and FIG. 9 represents a QT/TQ vs. RR distribution for a subject that is likely at high cardiac risk. In one embodiment, referring to FIG. 9, a non-linear function y(x) 901 is fit to a QT/TQ vs RR distribution using a least squares regression fit. In one embodiment function 901 is a polynomial. In some embodiment polynomial y(x) is a $2^{nd}$ or $3^{rd}$ degree polynomial. In some embodiments, curvature of nonlinear function 901 is computed using Formula 2. In one embodiment, the QT/TQ vs. RR distribution includes values obtained from a patient's ECG recording for a time period ranging from 10 minutes to 24 hours. A useful ECG recording can therefore be obtained in a clinic, emergency room, or at home while the patient goes about normal daily activities.

Curvature of non-linear function 901

$$\kappa = \frac{\frac{d^2 y}{dx^2}}{\left[1+\left(\frac{dy}{dx}\right)^2\right]^{3/2}}.$$  Formula 2.

In one example embodiment the curvature of function 901 is computed according to Formula 2 whereby curvature is measured using the first and second derivative of y(x). In some embodiments, curvature is evaluated for a range of RR values to gauge cardiac risk. The greater the absolute value of curvature over the selected range of RR values, the greater the degree of cardiac risk.

In one embodiment, maximum curvature of function 901 is computed for the selected range of RR values and compared to a threshold. In another embodiment, the mean of the curvature is computed for the selected range of RR values and compared to a threshold. In another embodiment, the slope of a line tangent to the point of maximum curvature is computed and the slope is compared to a threshold. In some embodiments, cardiac risk is gauged by noting the RR value at which maximum curvature occurs. The larger the RR value corresponding to maximum curvature, the higher the cardiac risk.

In some embodiments the selected RR range 902 is predetermined. In one embodiment, the selected RR range 902 is 400 to 1000 msec. In other embodiments, the selected RR range include RR values<the 25% percentile of RR values measured in a baseline recording for the patient. In another embodiment, the selected RR range includes RR values<the 50%. It is useful that the baseline recording include RR values obtained in a resting condition and when motor activity is elevated. In some embodiments, the time period for which the baseline recording is obtained includes ECG recorded when motion sensor 106 indicates that patient activity is within a predefined range.

In one embodiment the curvature of nonlinear function 901 is measured at a predetermined value of QT/TQ 903 and curvature is compared to a threshold as a metric of cardiac risk. In other embodiments, curvature is assessed at two or more values of QT/TQ and a mean value of curvature is computed from the two or more values. In one embodiment curvature is measured when QT/TQ=1. In other embodiments curvature is measured for larger values of QT/TQ (e.g. QT/TQ=1.5). In one embodiment point 902 is defined as the point at which QT/TQ is equal to a predetermined value. In one embodiment the predetermined value of point 902 is where QT/TQ is about 1. The higher the degree of curvature, the greater the cardiac risk.

Figure 6A:
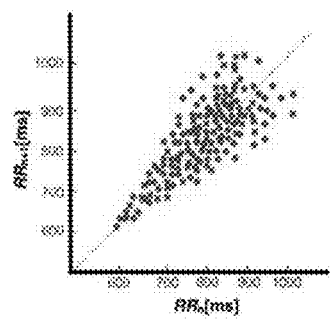
FIG. 6A provides a Poincare plot of an RR interval for normal and heart failure patients.
Figure 6B:
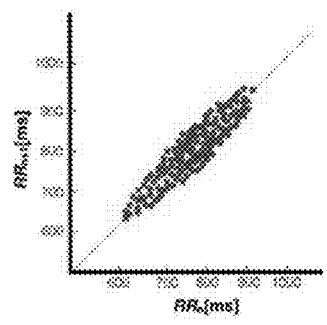
FIG. 6B provides a Poincare plot of an RR interval for normal and heart failure patients.
Figure 6C:
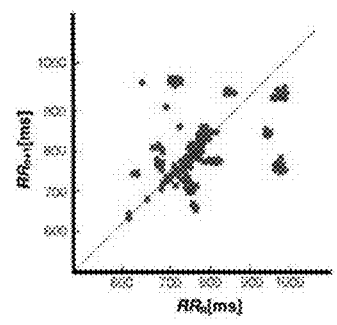
FIG. 6C provides a Poincare plot of an RR interval for normal and heart failure patients.

In another embodiment, characteristics of a Poincare plot of RR and QT are evaluated as a marker of CMND and cardiac risk. Referring to FIG. 6A, representing the Poincare plot of a normal individual, the shape of the Poincare plot resembles a comet with wider dispersion for longer RR intervals. In individuals at risk the Poincare plot develops a torpedo pattern with narrow dispersion or more complex patterns with individual clusters as shown in FIGS. 6B and 6C. FIGS. 6B and 6C represent Poincare plots for patients with heart failure. The abnormality in the Poincare plots described as torpedo pattern is driven by reduced overall HRV. The abnormality in the Poincare plot of 6C, characterized as a complex pattern, is driven by paradoxical increase in HRV as a result of erratic autonomic activity but would be characterized by a different set of parameters described above when error of fit is above threshold.

Figure 7:
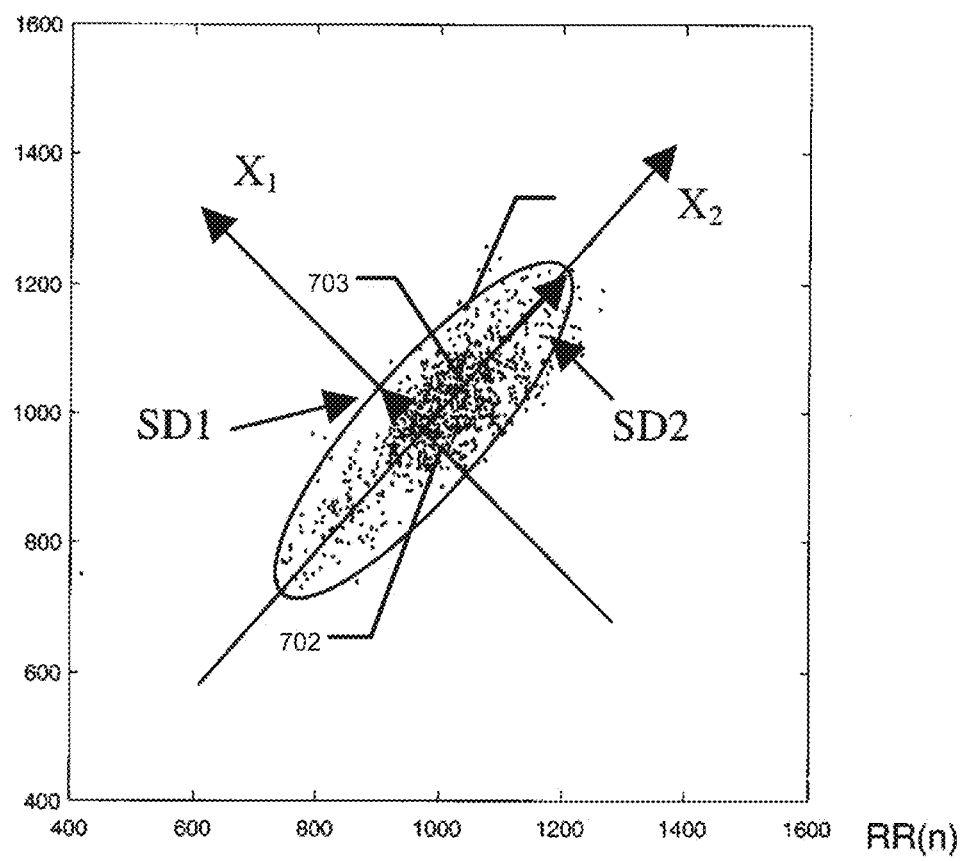
FIG. 7 provides illustration of quantitative characterization of a Poincare plot.

Referring to FIG. 7, in one embodiment an ellipse 701 is fitted to the Poincare plot and error of fit is measured. In one embodiment the error of fit (EOF) is computed by calculating norm of residuals. If calculated norm is >EOF threshold, it indicates that a more complex pattern is present. If error of fit is <=EOF threshold then length of axis 702 (SD1) and 703 (SD2) of the fitted ellipse are measured. The length of the axis 702 is equivalent to standard deviation of successive RR differences and thus represents short term heart rate variability. The length of axis 703 represents long-term variability of RR intervals. Hence the ratio of SD2/SD1 would increase in concert with cardiac risk. In one embodiment, the ratio of axes SD2/SD1 is compared to a threshold. If SD2/SD1<Thr2, then the Poincare plot has a torpedo-like shape. In some embodiments, characteristics of the ellipsoid and EOF are used to confirm or deny the accuracy of metrics derived from subcomponents. For example, if EOF is>a threshold, then autonomic tone is erratic and entropy of subcomponents corresponding to high frequencies is high and the patient is likely to be at cardiac risk.

In one embodiment, multiple metrics are combined to provide an indication of cardiac risk, degree of stress, or CMND. In one embodiment, metrics are combined in a linear combination. In one embodiment the weights for the linear combination are computed using logistic regression. In one embodiment, metrics are combined with other information. For example, atrial fibrillation (AF) burden is a common trigger of heart failure decompensation. In one embodiment, a measure of AF burden (AFb) is computed as the percentage of time the heart is in AF for a predetermined time. In one embodiment, if AFb is computed as a running mean of AF burden for the past 60 minutes. If AFb for a 60-minute interval is greater than a threshold (e.g. 25%, for example), then the patient is at risk of decompensating regardless of the value of any other metric. In the absence of AFb exceeding the predetermined threshold, risk is computed based upon one or more of the metrics described above. In one embodiment, the value of the threshold is based upon the patient's medical history as it relates to the AFb that has triggered decompensation events in the past.

Various embodiments may be implemented using one or more aspects as characterized in the following documents, which are fully incorporated herein by reference.
1. Beck A T, Ward C H, Mendelson M, Mock J, Erbaugh J. An inventory for measuring depression. *Arch Gen Psychiatry.* 1961; 4:561-571.
2. American Psychiatric Association, 2000. Diagnostic Criteria from DSM-IV-TR. American Psychiatric Association, Washington, D.C.
3. Woo M A, Stevenson W G, Moser D K, Trelease R B, Harper R M. Patterns of beat-to-beat heart rate variability in advanced heart failure. Am Heart J. 1992; 123:704-710.
4. Quintana D S, Heathers J A. Considerations in the assessment of heart rate variability in biobehavioral research. Frontiers in Physiology 2014
5. Pan, J. and Tompkins, W. J. 1985. A real-time QRS detection algorithm. IEEE Trans. Biomed. Eng.BME-32: 230-36
6. Gallnier, M et. al. Depressed low frequency power of heart rate variability as an independent predictor of sudden death in chronic heart failure. Eur. Hrt. J. 2000 vol 21,475-482.

What is claimed is:

1. A method comprising:
   computing a time series of cardiac intervals from a recording of activity of a beating heart of a subject;
   decomposing the time series into subcomponents;
   computing an envelope of at least one of the subcomponents; and
   determining a degree of mental stress of the subject based upon characteristics of the envelope.

2. The method of claim 1, wherein determining the degree of mental stress based upon one or more characteristics of the envelope includes detecting the presence of one or more of:
   a periodic component of a predetermined frequency;
   a time averaged mean energy in a first scale that exceeds a time averaged mean energy in a second scale for a specified time; and
   increased entropy in one of the subcomponents corresponding to a high frequency band.

3. The method of claim 1, wherein determining the degree of mental stress based upon one or more characteristics of the envelope includes evaluating a degree of randomness of fluctuations in energy of the time series over a predetermined time period.

4. The method of claim 3, wherein evaluating the degree of randomness of the fluctuations in energy includes computing entropy.

5. The method of claim 4, further including computing the metric of entropy using one of sample entropy and approximate entropy.

6. The method of claim 1, wherein computing a time series of inter-beat intervals includes:
   detecting a plethora of heart beats in the recording;
   computing a raw sequence of inter-beat intervals from consecutive ones of the detected beats;
   identifying invalid beats from the detected beats;
   creating a cleaned sequence of inter-beat intervals by excluding intervals computed using ones of the beats identified as being invalid; and
   resampling said cleaned sequence of inter-beat intervals to create an equispaced time series of inter-beat intervals.

7. The method of claim 6, wherein identifying invalid beats includes identifying invalid beats based on characteristics in the recording selected from the group of:
   ventricular arrhythmias;
   atrial fibrillation;
   characteristics indicating that a signal detected as a beat is not a beat; and
   noise beyond a noise threshold.

8. The method of claim 6, wherein identifying invalid beats includes identifying ectopic beats by:
   decomposing the recording into subcomponents;

detecting the presence of ventricular depolarizations in the subcomponents;

establishing a window around each detected ventricular depolarization;

computing the energy of high frequency and low-frequency subcomponents in each window;

computing, for each window, the ratio of low frequency energy to high frequency energy; and detecting the presence of an ectopic beat in a window based upon the computed ratio.

9. The method of claim 8, wherein computing high frequency energy in a window includes:

selecting one or more subcomponents corresponding to high frequency; and computing the high frequency energy using at least one of the sum of squares of the amplitude and the sum of the absolute values of the amplitude.

10. The method of claim 1, further including measuring the temperature of the subject, and detecting the presence of a CMND state based on the characteristics of the envelope and temperature of the subject.

11. The method of claim 1, further including measuring motor activity of the subject, wherein determining the mental stress includes evaluating characteristics of the activity measurements.

12. The method of claim 1, wherein the time series of cardiac intervals is comprised of at least one of the following:

RR intervals; and

QT intervals.

* * * * *

UNITED STATES PATENT AND TRADEMARK OFFICE
CERTIFICATE OF CORRECTION

PATENT NO. : 9,706,956 B2  
APPLICATION NO. : 15/144324  
DATED : July 18, 2017  
INVENTOR(S) : Brockway et al.

Page 1 of 1

It is certified that error appears in the above-identified patent and that said Letters Patent is hereby corrected as shown below:

In the Specification

Column 1, Line 4, Insert the following after the Title:
--STATEMENT REGARDING FEDERALLY SPONSORED RESEARCH AND DEVELOPMENT
This invention was made with government support under grant numbers R44DA011815 and R43HL110739 awarded by the National Institutes of Health. The government has certain rights in the invention.--

Signed and Sealed this
Eighteenth Day of March, 2025

Coke Morgan Stewart
*Acting Director of the United States Patent and Trademark Office*